United States Patent [19]

Floyd

[11] Patent Number: 4,766,221

[45] Date of Patent: Aug. 23, 1988

[54] N-ACYL SUBSTITUTED CYCLIC UREAS

[75] Inventor: William C. Floyd, Chester, S.C.

[73] Assignee: Sequa Chemicals, Inc., Chester, S.C.

[21] Appl. No.: 848,201

[22] Filed: Apr. 4, 1986

[51] Int. Cl.$^4$ ............................................. C07D 233/38
[52] U.S. Cl. .................................. 548/320; 548/319; 548/321
[58] Field of Search .................... 548/320, 319, 321

[56] References Cited

U.S. PATENT DOCUMENTS

| | | | |
|---|---|---|---|
| 2,613,212 | 10/1952 | Hurwitz et al. | 548/318 |
| 2,881,155 | 4/1959 | Hankins | 526/263 |
| 3,627,778 | 12/1971 | Nusslein et al. | 548/320 X |
| 3,728,451 | 4/1973 | Newallis | 514/94 |
| 4,104,220 | 8/1978 | Sims | 524/809 |
| 4,111,877 | 9/1978 | Dixon et al. | 524/809 |
| 4,138,398 | 2/1979 | Richter et al. | 540/492 |
| 4,151,142 | 4/1979 | Herman et al. | 524/530 |
| 4,217,436 | 8/1980 | Richter et al. | 528/45 |
| 4,376,189 | 3/1983 | Trivette | 524/219 X |
| 4,410,689 | 10/1983 | Barsa et al. | 528/367 |

FOREIGN PATENT DOCUMENTS

| | | | |
|---|---|---|---|
| 0080451 | 6/1983 | European Pat. Off. | 524/219 |
| 2088854 | 6/1982 | United Kingdom | 548/349 |

OTHER PUBLICATIONS

*Chemical Abstracts*, 95:25624f (1981), [Ger. Offen. 3,016,960, Toda et al., 11/13/80].
*Chemical Abstracts*, 89:109481w, (1978), [Geo. Offen. 2,652,004, May et al., 5/24/78].
*Chemical Abstracts*, 83:18150y, (1975), [Ger. Offen. 2,400,393, Schwarzer et al., 7/24/75].
*Chemical Abstracts*, 84:75116k, (1976), [Ger. Offen. 2,419,124, Schnee et al., 11/6/75].
*Chemical Abstracts*, 96:37013q, (1982), [JPN Kokai, JP 81,110,765, 9/2/81].
*Chemical Abstracts*, 70:68252j, (1969).
H. Ulrich et al., *J. Org. Chem.*, vol. 43, No. 8, 1978, pp. 1544-1546.
P. Sherwood, *J. Coating Technology*, vol. 54, No. 689, Jun. 1982, pp. 61-65.

*Primary Examiner*—Richard A. Schwartz
*Attorney, Agent, or Firm*—Mitchell D. Bittman

[57] ABSTRACT

N-acyl substituted cyclic ureas are prepared which are useful as blocked isocyanates in one-component polyurethane systems.

8 Claims, No Drawings

N-ACYL SUBSTITUTED CYCLIC UREAS

BACKGROUND

This invention relates to the preparation of novel cyclic ureas, and more particularly to N-acyl substituted cyclic ureas. These compounds are particularly useful either directly or as an intermediate to prepare a compound that can be copolymerized and used as a polymer crosslinker, more specifically functioning as a blocked isocyanate.

The formulation of one-component polyurethane forming systems which use "blocked" isocyanates are well known in the coating art. Upon heating the one-component system containing blocked isocyanates, free isocyanates are generated to react with the polyol to form the polyurethane. The need for storage in separate containers is eliminated since the system remains stable until heated.

However, the blocked isocyanates suffer from the disadvantage of volatile or fugitive blocking groups. These groups, often compounds such as phenol, alcohols and the like; are volatile at the curing temperature, and need to flash off, creating emissions problems. If the volatiles are entrained in the coating, they cause loss of strength. Bis-acyl cyclic ureas have been used as blocked isocyanates, and do not have the problem of volatile leaving groups, since the blocking group is part of the same molecule. These, however, do have a disadvantage of being difficult to disperse into the polyol, requiring such equipment as a ball mill. This mixing requirement may lead to non-homogeneous polymers.

We have now found a novel class of n-acyl substituted cyclic ureas which are particularly useful as blocked isocyanates in stable one-component polyurethane systems.

The prior art discloses a wide variety of substituted cyclic ureas which are useful for various purposes. U.S. Pat. Nos. 4,138,398, 4,217,436 and 4,410,689 disclose bis cyclic ureas which are useful as masked isocyanates and U.S. Pat. No. 4,111,877 discloses a N-cyclic ureido alkylamino derivative which is useful in imparting wet adhesion properties to water based paints. Other prior art disclosures of substituted cyclic ureas include U.S. Pat. Nos. 2,613,212, 2,881,155, 4,104,220 and 4,151,142.

SUMMARY

Briefly, this invention comprises a N-acyl substituted cyclic urea of the formula:

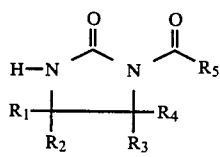

wherein $R_1$, $R_2$, $R_3$ and $R_4$ may be the same or different and each my be H, OH, COOH, R, OR or COOR, wherein R is an alkyl or substituted alkyl having 1 to 4 carbon atoms and wherein $R_5$ has 2 to 40 carbon atoms and is either an olefin, a carboxylic acid, an ester, a combination thereof, or a halogenated alkyl.

DETAILED DESCRIPTION

The starting material for the preparation of the N-acyl substituted cyclic ureas of the above formula is a cyclic urea corresponding to the formula:

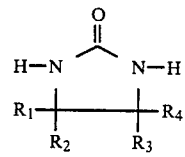

wherein $R_1$, $R_2$, $R_3$ and $R_4$ may be the same or different and each may be H, OH, COOH, R, OR or COOR, wherein R is an alkyl or substituted alkyl group having 1 to 4 carbon atoms.

Typical examples of cyclic ureas include 4,5-dihydroxy-2-imidazolidinone, 4,5-dimethoxy-2-imidazolidinone, 4-methyl ethylene urea, 4-ethyl ethylene urea, 4-hydroxyethyl ethylene urea, 4,5-dimethyl ethylene urea and the like. The preferred cylic urea is ethylene urea, i.e. wherein $R_1$, $R_2$, $R_3$ and $R_4$ are H, because of its ease of reactivity with anhydrides or acid chlorides, and lack of side reactions leading to by-products. The cyclic urea is reacted with various substituents to provide the N-acyl substituted cyclic urea wherein $R_5$ is either an olefin, a carboxylic acid, an ester or a halogenated alkyl substituent.

In one embodiment, the cylic urea is reacted with a cyclic anhydride which provides an N-acyl substituted cyclic urea with a carboxylic acid substituent. Typical cyclic anhydrides include maleic anhydride, succinic anhydride, dihydrophthalic anhydride, glutaric anhydride and alkenyl succinic anhydrides which provide an $R_5$ substituent which is a carboxylic acid, preferably wherein $R_5$ is —$CHR_6CHR_7COOH$, —$CR_6CR_7COOH$, —$(CH_2)_3COOH$ or

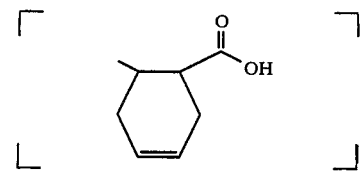

wherein $R_6$ and $R_7$ may be the same or different and is an H, or up to $C_{40}$ alkenyl. In a preferred embodiment ethylene urea is reacted with maleic anhydride in a polar aprotic solvent such as acetonitrile, dimethylsulfoxide or dimethyl formamide, to make cis-2-butenoic-4-oxo-4(1-imidazolidin-2-one) acid. In another preferred embodiment ethylene urea is reacted with succinic anhydride in dimethyl formamide to form 4-oxo-4-(1-imidazolidin-2-one)-1-butanoic acid.

An ester of the carboxylic acid may be prepared either by reaction with an alcohol or by reaction with a halogenated allyl to add olefin functionality. An ester of 4-oxo-4-(1-imidazolidin-2-one)-1 butanoic acid is prepared by reaction with aqueous potassium hydroxide, then allyl chloride in dimethyl formamide to make 4-oxo-4-(1-imidazolidin-2-one)-21-butanoic acid, allyl ester.

Conventional esterification calls for refluxing the acid in an excess of alcohol with an acidic catalyst. This was found to lead to cleavage of the imidazolidinone ring and further product decomposition. An alternate process was found which, in general, calls for slurrying the acid in an excess of alcohol, cooling the reaction mixture, and treating with an equivalent of thionyl chloride. The reaction mixture is slowly allowed to warm up whereupon HCl and $SO_2$ are evolved. These gases may be removed by purging with $N_2$ or dry air. The product may then be isolated by filtration, or whatever method is suitable for its physical state. This procedure can be used with any primary alcohol such as methanol, ethanol, propanol, n-butanol, allyl alcohol, isobutyl alcohol, 1,1-dihydroperflouro alkyl alcohols, ethylene glycol monoalkyl ethers, diethylene glycol monoalkyl ethers, ethoxylated phenol derivatives and the like to provide an $R_5$ substituent which is a methyl ester, ethyl ester, propyl ester, butyl ester, allyl ester, flourocarbon ester, alkoxyalkyl ester (e.g. methoxyethyl or ethoxyethyl ester), hydroxy alkyl ester, alkyl phenoxy (polyethoxy) alkyl ester or methallyl ester, of the carboxylic acid. These esters may be used to improve solubility in non-aqueous systems.

The olefin functionality allows for copolymerizing with monomers such as vinyl acetate and ethyl acrylate while the acyl cyclic urea functions as a blocked isocyanate which reacts with groups such as hydroxyl or amide under curing conditions. It is believed that the N-acyl substituted cyclic ureas act as crosslinkers by thermally dissociating during curing to an isocyanate and an amide, which then further reacts to cross-link the polymers. The n-acyl substituted cyclic ureas with olefin functionality could also be incorporated into vinyl or acrylic polymers to promote adhesion.

In another embodiment the $R_5$ substituent of the N-acyl substituted cyclic urea is substituted with a halogenated alkyl or an olefin which is obtained by reacting the cyclic urea with an unsaturated acid, such as acrylic acid, methacrylic acid or crotonic acid and thionyl chloride. This forms an acid chloride which acylates the cylic ureas, and adds HCL across the olefin to provide an $R_5$ which is a halogenated alkyl substituent wherein the halogen can be chloride, bromide or iodide, as in N-(1-oxo-3-chloro)propyl-2-imidazolidone. This reaction may be catalyzed by dimethyl formamide as with a Vilsmeier reagent. This N-acyl substituted cyclic urea may then be further reacted with, for example, triethyl amine, to remove the halogen and provide an $R_5$ substituent which is an olefin such as $-CH=CH_2$, $-CH=CHCH_3$ and $-CH=CH_2(CH_3)$ as with N-acryloyl ethylene urea.

EXAMPLE 1

Eighty-six grams (86 g) of ethylene urea (1 mole) was charged to a 1 liter 3-necked flask fitted with mechanical stirrer, condenser and thermometer. To this was added 250 ml of acetonitrile. This was heated to 50°-60° C. and stirred to form a white slurry. Maleic anhydride (98 g, 1 mole) was dissolved in 100 ml of warm acetonitrile and slowly added to the reaction. After 2-3 hours, the reaction was a clear amber. Upon cooling, most of the product precipitated and was filtered (approximately 60% of the theoretical yield). The acetonitrile solution was concentrated to recover the remainder of the product, 4(1-imidazolidin-2-one)-4-oxo-cis-2-butenoic acid. The product was recrystalized from isopropanol with a melting point of 150°-152° C. The IR spectrum showed N—H at 3300 cm$^{-1}$, c=o at 1705, c=o at 1670 cm$^{-1}$ and c=c at 640 cm$^{-1}$.

Alternatively, the ethylene urea and maleic anhydride were charged to the flask together, the solvent added, then heated at 50°-60° C. for 2-4 hours. The reaction was monitored by examining the reactions IR spectrum and observing the decrease of the anhydride peaks at 1850 cm$^{-1}$ and 1782 cm$^{-1}$. The general reaction temperature ranged from room temperature to 80°-100° C., but 50°-60° C. was preferred to minimize color generation.

EXAMPLE 2

To a 1 liter 3-necked flask equipped with a mechanical stirrer, thermometer and condenser was charged 114 g (1.3 moles) ethylene urea, 120 g dimethyl formamide and 120 g (1.2 moles) succinic anhydride. This was heated at 90° C. for 30 hours, at which time IR showed no anhydride peak. The product formed at this stage was 4-oxo-4-(1-imidazolidin-2-one)-1-butanoic acid. The reaction may also be catalyzed by tertiary amines such as 1,4-diazabicylooctane and dimethylaminopyridine. The product was characterized by IR (KBr) 3260, 1740, 1710, 1685, 1380, 1255 cm$^{-1}$; HNMR (DMSOd$_6$)$\delta$9.8 (br, s) 1),$\delta$7.35 (br, s, 1), $\delta$3.85-3.1 (AA'BB' mult. (ring), 4), $\delta$3.2-2.3 (AA'BB' mult., 4) and a m.p. of 130°-134° C.

EXAMPLE 3

The reaction of Example 2 was cooled to 40° C. and 150 g (1.2 moles) of 45% aqueous potassium hydroxide was slowly added by drip funnel. The resulting slurry was cooled to room temperature and allowed to stir one hour. The slurry was filtered, washed with isopropanol and allowed to air dry. The salt cake was returned to the same flask and slurried with 400 g of dimethyl formamide. The flask was set up for vacuum distillation with a water aspirator to remove moisture, and stripped up to 85° C. About 100 ml of distillate was collected. The reaction was cooled to 40° C. and 140 g (1.8 moles) of allyl chloride was slowly added along with 0.05 g potassium iodide as catalyst. The reaction was refluxed for 24 hours with the final reflux temperature being 86° C. At this time the IR showed no carboxylate peaks. The reaction was a clear tan solution with a potassium chloride precipitant. This was vacuum stripped to remove solvent and filtered to remove salt. The liquid was taken up in methylene chloride and washed with brine, saturated sodium bicarbonate and again with brine. Solvent was removed to afford a yellow oil which crystallized. The crystals were filtered and washed with water to give 150 g (55% yield) of a white granular product which was 4-oxo-4-(1-imidazolidin-2-one)-1-butanoic acid, allyl ester with an IR (KBr) of 3260, 1740, 1730, 1680, 1395, 1160 cm$^{-1}$; HNMR (CDCl$_3$)$\delta$6.30 (br, s,1),$\delta$6.1-5.5 (mult., 1),$\delta$5.35 (mult., 1),$\delta$5.05 (mult., 1), $\delta$4.45 (d,J=5 Hz, 2),$\delta$4.10-3.6 (AA'BB' mult. (ring), 4), $\delta$3.40-2.50 (AA'BB' mult., 4) and a m.p. OF 69°-71° C.

EXAMPLE 4

To a 100 ml flask equipped with a stir bar, condenser and thermometer was charged 9.5 g (0.11 moles) of ethylene urea, 0 g (0.10 moles) of succinic anhydride and 10g dimethylsulfoxide (DMSO). This was heated at 75°-80° C. for 20 hours until the anhydride peak was not observable by IR. The reaction was cooled to 40°-45° C. and 11.8 (1.05 equivalents) of potassium t-butoxide was slowly added, causing the reaction to thicken. This was stirred for 4 hours at 65° C. To this was added 0.01 g of potassium iodide for catalyic purposes, and 8.4 g (0.11 moles) allyl chloride slowly by drip funnel. The reaction was heated to 75°-85° C. for 4 hours when the IR showed no carboxylate peak. This was filtered, taken up in methylene chloride, washed with brine and concentrated to give an oil which crystallized similar to that in Example 3. The product obtained in moderate yield was identical to the product of Example 3.

EXAMPLE 5

To a dry 100 ml round bottomed flask fitted with a stir bar, thermometer, Claisen tube, addition funnel and nitrogen inlet was added 18.4 g (0.1 moles) of the reaction product of ethylene urea and maleic anhydride (4(1-imidazolidin-2-one)-4-oxo-cis-2-butenoic acid) and 30 g methanol. This was stirred rapidly, giving a white slurry, and cooled in an ice bath to 0° C., and maintained under a nigrogen blanket. To the addition funnel was charged 13.1 g (0.11 moles) of thionyl chloride. This was slowly added dropwise, so that the reaction temperature remained below 5° C. After the addition was complete, the reaction remained in the ice bath for 30 minutes and was then allowed to warm to room temperature. As the reaction warmed, it became thicker, finally solidifying after about 1 hour. The methyl ester product was filtered, washed with cold methanol and allowed to air dry, yielding 20.6 g white solid which was 4(1-imidazolidin-2-one)-4-oxo-cis-butenoic acid methyl ester having a melting point of 90°–92° C., IR (KBr): 3240 cm$^{-1}$ (NH), 1750 cm$^{-1}$ (c=o), 1720 cm$^{-1}$, 1670 cm$^{-1}$ (c=o), 1644 cm$^{-1}$ (c=c); HNMR (DMSOd$_6$): δ8.15 (1H,dJ=15H$_z$),δ7.8 (1h,brs) δ6.55 (1H,d,J=15 H$_z$),δ3.7 (3H, S),δ3.55 (4H,AA'BB' mult.).

EXAMPLE 6

To a dry 250 ml 3-necked flask equipped with a mechanical stirrer, condenser, N$_2$ balloon and thermometer was added stirrer 19.5 g maleic anhydride (0.2 moles) and 55 g methylene chloride. This was stirred and heated gently to absorb the endotherm and help the anhydride to dissolve. To this was added 17.2 g (0.2 moles) ethylene urea, and heated to reflux until the IR showed no anhydride peaks (approximately 16 hours). To the white suspension in methylene chloride was added 50 g methanol. This slurry was cooled with stirring in an ice bath to 0° C. An addition funnel was attached to the flask and charged with 26.2 g (0.22 moles) of thionyl chloride. This was added slowly so that the temperature remained below 5° C. The reaction was stirred for 1 hour in the ice bath after addition was complete and was then allowed to warm to room temperature. A nitrogen sparge was started and the reaction was stirred at room temperature for 2 hours. The product was filtered and washed with cold methanol. After drying on the filter, 34.3 g of white crystaline solid was recovered (87% yield). This was the same methyl ester obtained in Example 5.

EXAMPLE 7

The same procedure was followed as in Example 5, except that the alcohol was varied from methanol to ethanol, propanol and butanol. The following results were obtained:

ethyl ester: mp of 120° C.; IR (KBr): 3275 cm$^{-1}$ 1770 cm$^{-1}$(c=o), 1719 cm$^{-1}$(c=o), 1663 cm$^{-1}$(c=o), 1635 cm$^{-1}$ (c=c): HNMR (CDCl$_3$) δ8.20 (1H,d,J=15H$_z$),δ6.80 (1H,d,J=5H$_z$), δ6.40 (1H, br), δ4.20 (2H,q,J=7H$_z$), δ3.70(4H, AA'BB' mult.) δ1.30 (3H,t,J=7H$_z$) propyl ester: mp of 85°–88° C.; IR (KBr): 3270 cm$^{-1}$ (NH), 1740 cm$^{-1}$ (c=o), 1718 cm$^{-1}$ (c=o), 1668 cm$^{-1}$ (c=o), 1638 cm$^{-1}$(c=c). HNMR (CDCL$_3$) δ8.20 (1H,d,J= 15H$_z$), δ6.79 (1H,d,J=5H$_z$),δ6.45 (1H br),δ4.10 (2H t J=7H$_z$). δ3.70 (4H AA'BB' mult.) δ16.9 (2H sextet, J=7H$_z$), δ0.95 (3H,t,J=7H$_z$).

EXAMPLE 8

To a dry 100 ml 3-necked flask equipped with a magnetic stirring bar, reflux condenser and addition funnel was charged 8.6 g (0.10 mole) ethylene urea, 8.9 g (0.11 mole) glacial acrylic acid and 50 ml methylene chloride. This was stirred to give a translucent suspension. To the addition funnel was charged 12 g (0.11 mole) thionyl chloride. After stirring 30 minutes at room temperature, the thionyl chloride was added dropwise over a 45 minute period. As the additions approached the half way point, a white precipitate was observed in the flask. There was an exotherm and light reflux with a vapor temperature of 39° C. was observed. The odor of SO$_2$ was also detected, and the evolving vapor caused litmus paper to turn red. The reaction was stirred without heating for 1 hour after the addition was completed, then gently heated to reflux. After refluxing about 12 hours, the solution had become yellow and almost clear. The reaction was filtered, and solvent evaporated to give a waxy pale yellow solid. This washed with methanol to give a white waxy solid which was N-1-oxo-3-chloropropyl ethylene urea, 52% yield, mp 111°–112° C., IR (KBr) 3260 cm$^{-1}$, 1733 cm$^{-1}$, 1676 cm$^{-1}$, 390 cm$^{-1}$, 1265 cm$^{-1}$, 1060 cm$^{-1}$, 755 cm$^{-1}$, 655 cm$^{-1}$.

This product was dissolved in 50 ml of dry methylene chloride and mixed with 1.1 equivalents of triethyl amine. The reaction was stirred overnight forming a white precipitate of triethylammonium hydrochloride. The reaction was filtered and concentrated to form a white solid, N-acryloyl ethylene urea, 80% yield. IR (KBr): 3260 cm$^{-1}$, 1735 cm$^{-1}$, 1645 cm$^{-1}$, 1612 cm$-1$, 1260 cm$^{-1}$, 1070 cm$^{-1}$, 960 cm$^{-1}$.

EXAMPLE 9

To demonstrate blocked isocyanate reactivity a 0.5 g portion of N-acryloyl ethylene urea was mulled with 5 drops of glycerin to give a white paste. A thin film IR spectrum showed broad OH (glycerin) carbonyl (1725, 1670 cm$^{-1}$) and strong C=O (1105, 1040 cm$^{-1}$, glycerin). A small portion was placed in an aluminum sample pan for a differential scanning calorimeter (Perkin-Elmer DSC-1B). The sample was scanned at a rate of 10° C. per minute from 300° K. (27° C. ) to 450° K. (177° C.). An exothermic peak was noted beginning at 388° K. (115° C.) and ending at 414° K. (141° C.) Upon cooling, a clear, tacky syrup was obtained. The IR spectrum of this product was different from the original mull. The —OH and C—O peaks from the glycerin were much weaker. The carbonyls shifted from 1725 to 1730 cm$^{-1}$ and 1670 to 1680 cm$^{-1}$ and were relatively more intense insert and a very prominent urethane ester c—o— appeared at 1270 cm$^{-1}$ that was absent in the original spectrum. These results, particularly the formation of the urethane ester peak at 1270 cm$^{-1}$ are interpreted to mean that between 115° C. and 141° C., the cyclic urea cleaves to an isocyanato ethylene amide which then reacts with the glycerin. Similar reactivity would be expected if the monomer were copolymerized through its double bond.

This monomer is expected to find uses in two broad categories. First, it could be used to introduce a blocked isocyanate into a polymer. The polymer could be aqueous solution, solvent solution or emulsion, which is generally radical catalyzed.

Second, it could be used to incorporate a terminal activated olefin into a molecule by inducing ring cleavage in the presence of active hydrogen sources (OH-,—NH,—SH). Such compounds are used in UV, electron beam and radiation cure coatings. The activated olefin can also be incorproated by reaction of the ring N—H and an aldehyde (e.g. formaldehyde) with a suitable substrate, leaving the ring intact.

EXAMPLE 10

To a dry 250 ml 3-necked flask equipped with a mechanical stirrer, addition funnel, thermometer and condenser was charged ethylene urea (17.2 g, 0.2 moles), acrylic acid (16 g, 0.22 moles) and 100 g of methylene chloride. This was stirred at room temperature for 15 minutes giving a hazy gray suspension. To the addition funnel was charged thionyl chloride (25 g, 0.21 moles). The thionyl chloride was added drop-wise over a forty minute period with the temperature rising to 35° C. Midway through the addition a white precipitate formed. The reaction was refluxed for 12 hours and filtered. The reaction was washed with brine and concentrated to a pale yellow wax which was N-(1-oxo-3-chloro)propyl-2-imidazolidone (synonym: β-chloropropionyl ethylene urea) (31g, 88% yield) IR (KBr): 3260, 1730, 1676, 1380, 265 cm$^{-1}$.

In this Example thionyl chloride and acrylic acid are used to make acryloyl chloride in situ. Acryloyl chloride could be used directly in place of the acrylic acid and thionyl chloride. If, instead of acrylic acid, methacrylic acid is used, the corresponding methacryloyl derivatives are obtained.

EXAMPLE 11

To a dry 100 ml 3-necked flask equipped with a stir bar, condenser and addition funnel was added 60 g methylene chloride and 17.6 g (0.1 moles) of N-(1-oxo-3-chloro)propyl-2-imidazolidone (the product of Example 10). This was stirred to form a cloudy suspension. Triethyl amine (13 g, 0.13 moles) was slowly added by addition funnel. The resulting clear amber solution was refluxed about 4 hours until IR showed the reaction to be complete. During the reflux a white precipitant (triethylamine hydrochloride) formed. The reaction was filtered and washed with brine and saturated sodium bicarbonate. The pale yellow solution was then concentrated to yield 11g (78%) white wax which was N-(1-oxo-2-propene)-2-imidazolidone (synonym: acryloyl ethylene urea) with an IR (KBr): 3260, 1738, 1648, 1620, 1425, 1350, 1265 cm$^{-1}$; 1HNMR (DMSOd$_6$) δ7.65 (br, s,1), δ7.48 (dd,$J^B$x=11 Hz, $J_{AX}$=17 Hz, 1), δ6.15 (dd, $J_{AX}$=17 Hz , $J_{AB}$=3hZ, 1), δ5.70 (dd, $J_{AB}$=3 Hz, $J_{BX}$=11 Hz, 1), δ3.95–3.15 (AA'BB' mult., 4).

EXAMPLE 12

A solution polymer was prepared by placing into a dry flask ethyl acetate (176.5 g), ethyl acrylate (100 g), hydroxy ethyl acrylate (2.9 g), 4-(1-imidazolidin-2-one)-4-oxo-cis-2-butenoic acid, ethyl ester (85 g) and dodecyl mercaptan (7.5 g). This was agitated with a nitrogen sparge for 30 minutes and heated to 37° C. whereupon 1375 g of azobisisobuteronitrile catalyst (Vazo ® 64 by DuPont) was added. A solution containing 75 g of ethyl acetate and 55.1 g of hydroxyethyl acrylate was added by drip funnel over 30 minutes. After the addition was complete, the reaction was heated to 50°–55° C. for 2 hours. Solvent was then stripped to afford a thick, pale yellow syrup.

When dried for 30 minutes at 105° C., the product formed a tacky syrup that redissolved in ethyl acetate. When mixed with a catalyst such a p-toluene sulfonic acid or dibutyl tin dilaurate, the product dried under similar conditions formed a clear, amber, rubbery film which adhered tenaciously to the aluminum pan which contained it. These rubbery catalyzed films did not redissolve in ethyl acetate. This demonstrates the crosslinking system. Such technology would be useful in areas such as coatings, enamels, adhesives or paints.

What is claimed is:

1. A N-Acyl substituted cyclic urea of the formula

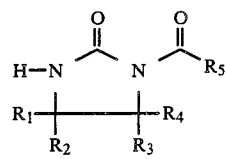

wherein $R_1$, $R_2$, $R_3$ and $R_4$ may be the same or different and each may be H, OH, COOH, R, OR or COOR, wherein R has 1 1 to 4 carbon atoms and is an alkyl or substituted alkyl group and wherein $R_5$ has 2 to 40 carbon atoms and is an olefin consisting of —CH=CH$_2$, a saturated aliphatic alkyl carboxylic acid, a halogenated alkyl, or an ester of a carboxylic acid chosen from the group consisting of CHR$_6$CHR$_7$COOH, (CH$_2$)$_3$COOH, CR$_6$CR$_7$COOH, wherein R$_6$ and R$_7$ may be the same or different and is an H or up to C$_{40}$ alkenyl and

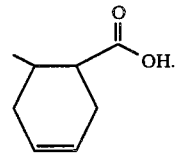

2. Cyclic urea of claim 1 wherein $R_1$, $R_2$, $R_3$, and $R_4$ are H.

3. Cyclic urea of claim 1 wherein $R_5$ is halogenated alkyl wherein the halogen is chosen from the group consisting of Cl, Br and I.

4. A N-Acryl substituted cyclic urea of the formula

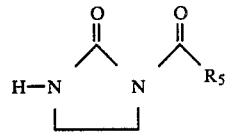

wherein $R_5$ has 2 to 40 carbon atoms and is an ester of a carboxylic acid chosen from the group consisting of CHR$_6$CHR$_7$COOH, (CH$_2$)$_3$COOH, CR$_6$CR$_7$COOH, wherein R$_6$ and R$_7$ may be the same or different and is an H or up to C$_{40}$ alkenyl and

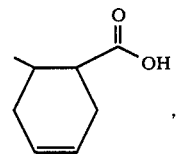
, with the ester being chosen from the group consisting of a methyl ester, ethyl ester, butyl ester, propyl ester, allyl ester, flourocarbon ester, alkoxy alkyl ester, hydroxy alkyl ester, alkyl phenoxy (polyethoxy) alkyl ester and methallyl ester.

5. 4-oxo-4-(1-imidazolidin-2-one)-1-butanoic acid.
6. 4-oxo-4-(1-imidazolidin-2-one)-1-butanoic acid allyl ester.
7. N-acryloyl ethylene urea.
8. (N-(1-oxo-3-chloro)propyl)imidaizolidin-2-one.

* * * * *